(12) United States Patent
Markussen

(10) Patent No.: US 7,740,618 B2
(45) Date of Patent: Jun. 22, 2010

(54) SYRINGE DEVICE

(75) Inventor: Tom Hede Markussen, Bagsvaerd (DK)

(73) Assignee: Novo Nordisk A/S, Bagsvaerd (DK)

( * ) Notice: Subject to any disclaimer, the term of this patent is extended or adjusted under 35 U.S.C. 154(b) by 173 days.

(21) Appl. No.: 11/665,166

(22) PCT Filed: Oct. 13, 2005

(86) PCT No.: PCT/DK2005/000659

§ 371 (c)(1), (2), (4) Date: Oct. 1, 2007

(87) PCT Pub. No.: WO2006/039930

PCT Pub. Date: Apr. 20, 2006

(65) Prior Publication Data

US 2008/0097322 A1    Apr. 24, 2008

Related U.S. Application Data

(60) Provisional application No. 60/626,512, filed on Nov. 10, 2004, provisional application No. 60/677,938, filed on May 5, 2005.

(30) Foreign Application Priority Data

Oct. 14, 2004 (DK) .............................. 2004 01576
Apr. 26, 2005 (EP) ................................. 05009101

(51) Int. Cl.
*A61M 5/00* (2006.01)
(52) U.S. Cl. ...................................... 604/208; 604/135
(58) Field of Classification Search ................. 604/135, 604/208
See application file for complete search history.

(56) References Cited

U.S. PATENT DOCUMENTS

| 4,865,591 | A | * | 9/1989 | Sams | .......................... 604/186 |
| 4,973,318 | A | | 11/1990 | Holm et al. | |
| 5,626,566 | A | * | 5/1997 | Petersen et al. | ............. 604/208 |
| 6,371,939 | B2 | * | 4/2002 | Bergens et al. | .............. 604/156 |
| 6,413,242 | B1 | * | 7/2002 | Michel et al. | ................ 604/187 |
| 2002/0120235 | A1 | * | 8/2002 | Enggaard | .................... 604/135 |

FOREIGN PATENT DOCUMENTS

| WO | WO 94/22507 | 10/1994 |
| WO | WO 99/03522 | 1/1999 |
| WO | WO 99/38554 | 8/1999 |
| WO | WO 03/038806 A1 | 5/2003 |
| WO | WO 2004/028598 A1 | 1/2004 |

* cited by examiner

*Primary Examiner*—Nicholas D Lucchesi
*Assistant Examiner*—Gerald Landry, II
(74) *Attorney, Agent, or Firm*—Marc A. Began

(57) ABSTRACT

A ratchet-free and gear-free one-to-one mechanism for setting a dose in a syringe device comprising a dose setting member adapted to be rotated along a piston rod with a threaded outer surface so as to set a dose to be ejected.

During dose setting the piston rod is locked such that rotational movement of the dose setting member does not result in rotational movement of the piston rod.

During dose ejection the piston rod and the dose setting member are locked in relation to each other such that translational movement of the dose setting member causes relative rotational and translational movement of the piston rod.

22 Claims, 14 Drawing Sheets

SYRINGE DEVICE

CROSS-REFERENCE TO RELATED APPLICATIONS

This application is a 35 U.S.C. §371 national stage application of International Patent Application PCT/DK2005/000659 (published as WO 2006/039930), filed Oct. 13, 2005, which claimed priority of Danish Patent Application No. PA 2004 01576 filed Oct. 14, 2004 and European Patent Application 05009101.6, filed Apr. 26, 2005; this application further claims priority under 35 U.S.C. §119 of U.S. Provisional Applications 60/626,512, filed Nov. 10, 2004 and 60/677,938 filed May 5, 2005.

FIELD OF THE INVENTION

The present invention relates to a syringe device which is primarily intended for domestic use, the syringe device comprising a dose setting member adapted to be rotated along a piston rod with a threaded outer surface so as to set a dose to be ejected. In particular, the present invention relates to a syringe device wherein the piston rod is locked for rotation in relation to a first member of the syringe device and wherein a second member, additionally, may be rotated along the piston rod so as to retain the piston rod in a direction opposite the ejection direction.

BACKGROUND OF THE INVENTION

When drugs are to be injected into the human body, it is often essential that the dose to be injected is set with a high precision, as a too high or too small dose can have undesirable consequences. At the same time, it should be easy for the patient to set the dose, especially as many patients have poor dexterity. Thus, it is desirable to provide a syringe device wherein the dose is set with a gear mechanism, such that a relative large displacement of a dose setting member results in a relatively small increase or decrease of the set dose.

One such system is known from WO 99/38554, wherein the dose is set by manually rotating an injection button, whereby the button is screwed outwards from the housing. In its movement outwards, the injection button will draw the dose scale drum with it. When the injection button is pressed the movement of this button is transformed into a rotation of the piston rod. The piston rod has an external thread mating an internal thread of a central bore in a wall closing the housing. The threads are designed so that rotation of the piston rod will drive the rod into an ampoule.

Another system is known from WO 2004/028598, which discloses an injection device comprising threaded drive rod in engagement with threads of a rear section of a container holding housing. A lock nut is arranged on the drive rod so as to be slidable but rotationally fixed in relation to the drive rod. A spring is arranged between an end surface of the lock nut and an interior ledge of a dose nut, which comprises a second section having threads on its inner surface in engagement with the threaded drive rod. The force from the spring between the lock nut and the dose nut urges the dose nut away from the lock nut.

Further systems may be seen in US 2002/120235, U.S. Pat. No. 6,413,242, WO 99/38554, WO 94/22507, EP 0 338 806 and U.S. Pat. No. 4,973,318.

In the treatment of certain decreases, e.g. diabetes, patients must perform injections of a drug, such as insulin, on a daily basis. However, such injections can be painful due to the penetration of the needle through the patient's skin and possibly other tissue. Accordingly, syringe devices with thin needles have been developed. However, a small cross-section in the needle, i.e. a narrow passage for the drug, requires a large injecting force. Patients suffering from poor dexterity may not always be able to bring about a large injecting force, or may not feel comfortable providing the required injecting force.

It is thus an object of preferred embodiments of the present invention to provide a syringe device, wherein the injection mechanism does not add to the resistance in the drug ejection system, i.e. in which there is as little resistance in the injection mechanism as possible. Furthermore, it is an object of a preferred embodiment of the present invention to provide a syringe device making it easy for the patient to set a dose with a high precision, even if the patient's dexterity is poor.

A further object of a preferred embodiment of the present invention is to provide an injection assisting system for providing an injection force for assisting an operator in performing an injection.

Additionally, it is an object of a preferred embodiment to provide a syringe device, wherein the piston may be locked for movement in a direction opposite to direction of injection, such that air is not sucked into the drug reservoir by drawing the piston backwardly. Yet another object of a preferred embodiment of the present invention is to provide a syringe device wherein it is possible to decrease a set dose prior to injection, in case a too high dose has been set by mistake.

Furthermore, it is an object of a preferred embodiment of the present invention to provide a syringe device which provides a tactile feedback to the user of the progress of an injection process.

SUMMARY OF THE INVENTION

In a first aspect the present invention provides a syringe device comprising:
- a housing;
- a piston rod having a threaded outer surface, the piston rod being retained in relation to a first member in such a way that no relative rotation of the piston rod and the first member is possible and in such a way that the piston rod can slide longitudinally relative to the first member;
- a dose setting member defining a passage for the piston rod, the passage having a threaded inner surface for engagement with the threaded outer surface of the piston rod, so as to define a connection between the dose setting member and the piston rod, the dose setting member being arranged with respect to the piston rod such that rotation of the dose setting member causes the dose setting member to be displaced longitudinally along the piston rod, whereby a stroke length of the piston rod is defined by the longitudinal displacement of the dose setting member in a proximal direction relative to a predetermined position of the dose setting member, and such that a translational displacement of the dose setting member relative to the housing is transmittable via said connection into a translational displacement of the piston rod relative to the housing;
- a second member defining a passage for the piston rod the passage having a threaded inner surface for engagement with the threaded outer surface of the piston rod, and;
- a first locking means for locking the first member and second member against relative rotation, so that no displacement of the piston rod in the proximal direction is possible, when the first locking means is in its locking position, a spring which is arranged to bias the second member and the dose setting member towards each other, such that when the dose setting member is rotated and thereby displaced longitudinally along the piston rod, the spring is strained, and such that translational displacement of the dose setting member and the piston rod in the distal direction to eject the dose unstrains the spring, whereby energy accumulated during straining of the spring is released to provide said ejection force.

The present invention comprises four key elements; the piston rod, the dose setting member, first member and the second member. The elements may be arranged in different ways while achieving the same result. During use two situations occur; a dose setting situation and a dose ejection situation.

The four elements serve different purposes and have different characteristics, depending on the two situations, see further below:

The piston rod has a threaded outer surface, which engages a corresponding threaded inner surface of both the dose setting member and the second member. Furthermore, the piston rod comprises means e.g. a groove or a slot, which is used to lock the piston rod and the first member against relative rotation.

The dose setting member comprises a threaded inner surface which is adapted to engage the threaded outer surface of the piston rod.
  In the dose setting situation, the function of the dose setting member is to set a dose to be ejected. This is done by rotating the dose setting member along the piston rod.
  In the dose ejecting situation, the function of the dose setting member is to transfer a translational movement of the dose setting member to the piston rod, by means of the engagement of the threads.

The first member is locked against rotational movement in relation to the piston rod, however they are do not lock each other for translational movement.
  In the dose setting situation, the function of the first member (together with the second member and the piston rod) is to ensure that rotation of the dose setting member does not result in rotation of the piston rod. This is ensured by locking the first member and the second member against relative rotational movement.
  In the dose ejecting situation, the function of the first member is to ensure that translational movement of the dose setting member does not result in rotation of the dose setting member relative to the piston rod. This is done by locking the dose setting member and the first member for relative rotational movement.

The second member comprises a threaded inner surface which is adapted to engage the threaded outer surface of the piston rod.
  In the dose setting situation, the function of the second member together with the first member to ensure that the piston rod is not rotated when the dose setting member is rotated during dose setting.
  In the dose ejecting situation, the function of the second member is to move relatively to the piston rod (unlike the first member and the dose setting member), such that when the dose has been ejected, the piston rod may again be locked for relative rotational movement when a dose is set.

As described above, two situations occur during use:
In the dose setting situation the piston rod, the first member and the second member are all locked in relation to each other such that rotational movement of the dose setting member does not result in rotational movement of the piston rod. Thus, the piston rod remains fixed when a dose is set by rotating the dose setting member.

In the dose ejection situation the piston rod, the first member and the dose setting member are all locked in relation to each other such that translational movement of the dose setting member causes relative rotational and translational movement of the piston rod and the second member. Thus, a dose may be ejected where after the first and second member may be locked in relation to each other in the new position, such that when a further dose is set, the piston rod is be retained as described above under the dose setting situation.

One advantage of the present invention is that no gear mechanism is needed and thus the user will experience a "one to one" injection. By "one to one" is meant that the distance the button travels is equal to the distance the piston travels as no gear mechanism is provided. A further advantage is that a linear ratchet mechanism on the piston rod is avoided. This is advantageous as such mechanisms must be very precise when a "one to one" movement is performed as the traveled distance in some cases is very small such as a tenth of a millimeter or even less. In the present invention such small distances may be set by providing a small pitch.

As the dose is set by rotating the dose setting member along the piston rod, the translational displacement per turn of the dose setting member, and thereby the precision of the dose setting, is dependent from the pitch of the tread of the piston rod. Accordingly, embodiments for high-precision applications may be provided with a low pitch, whereas embodiments for less demanding applications may incorporate a piston rod defining a higher pitch.

Furthermore, as rotation of the dose setting member may be performed in both directions ("dial up" and "dial down"), it is possible to regret a dose set by rotating the dose setting member backwards, towards the predetermined position of the dose setting member.

In the present context, the term 'distal' designates that end of the device at which drug is ejected, i.e. usually the needle end of the device. The term 'proximal' designates the opposite end of the device. Accordingly, the piston and the piston rod move in the distal direction when an ejection is performed.

Also in the context of the present invention, there is distinguished between 'ejection' and 'injection'. By 'ejection' is meant that a dose of the drug is ejected out of the syringe, but not necessarily injected into the body of the patient. Whereas 'injection' means that a dosage of the drug is ejected out of the syringe and into the body of a patient.

In order to allow the piston rod to be rotationally locked in relation to the first member, the piston rod may have a cross-sectional shape which enables such locking. For example, the cross section of the piston rod may define two opposed flattened surface portions extending the length of the piston rod or at least a portion thereof, with the non-flattened surfaces defining segments of a circle and being threaded. The first member, or another member which is rotationally secured to the first member, may define co-operating inner surfaces which are adapted to engage the flattened surface portions of the piston rod. Such co-operating inner surfaces may e.g. be provided by a passage in the first member. The co-operating inner surfaces may be provided in that part of the first member which also defines the stop surface, e.g. an inwardly projecting collar portion in the first member.

In another embodiment, the entire outer surface of the piston rod is threaded, and a rotation prohibiting means is provided as one or more nuts on the piston rod. The nut(s)

is/are retained in relation to the outer surface of the piston rod, and the outer surface of the nut(s) is/are adapted to engage co-operating inner surfaces of the first member, so as to rotationally lock the piston rod relative to the first member.

In order to enhance the precision of the dose to be ejected, the fit between the thread of the dose setting member and the thread of the piston rod is preferably essentially slack-free. The interconnection between the second member and the piston rod is preferably also essentially slack free.

By rotating the dose setting member along the piston rod, the dose is set, the stroke length of the piston rod being defined by the longitudinal distance between a distal surface of the dose setting member and the predetermined position, the predetermined position being preferably defined by an abutment surface for the distal surface of the dose setting member. When the dose setting member is in the predetermined position, the distal surface of the dose setting member is thus preferably locked against displacement in the distal direction. The abutment surface for the dose setting member may be provided on a proximal surface of the aforementioned inwardly projecting collar portion in the first member. Alternatively, the abutment surface may be provided as another inwardly projection collar or flange portion in the first member.

Thanks to the threads of the piston rod and the dose setting member, the dose setting member's translational displacement may be transmitted to the piston rod. The user may apply an ejecting force directly to the dose setting member or to a separate member provided at the proximal side of the dose setting member. In yet another embodiment, the ejection is performed by application of a force directly to a portion of the piston rod, e.g. an end portion.

In order to assist patients with poor dexterity, who cannot easily provide the desired force to a syringe device, the device may comprise an ejection assisting system for providing an ejection force for assisting an operator of the device in forcing the piston in the distal direction so as to eject a dose. In one embodiment, the ejection assisting system is arranged to store potential energy in the device when the dose is set. Accordingly, the resistance felt when setting the dose will be larger, however, the force to be overcome when ejecting the dose will be smaller. When a dose is to be ejected, the potential energy is released, such that the force applied by the user needs not to be as high as if no ejecting assisting system were provided. In some embodiments, the assisting force is so high that the ejecting force required to be provided by the user is close to zero or even zero. In the latter embodiments, the ejection assisting system is adapted to force the piston in the distal direction, so as to eject the dose, without the aid of the user, when the user has initiated the ejection.

The potential energy may be stored by compressing a spring which is arranged to bias the second member and the dose setting member towards each other, such that when the dose setting member is rotated, and thereby displaced longitudinally along the piston rod, the spring is strained, and such that translational displacement of the dose setting member and the piston rod in the distal direction to eject the dose unstrains the spring, whereby energy accumulated during straining of the spring is released to provide said ejection force. The spring may be strained in its longitudinal direction either by compressing or expansion. When the spring is stainable in the longitudinal direction, the spring and the dose setting member may be able to slide in relation to each other, such that the spring is not twisted when the dose setting member is rotated to set a dose.

Alternatively, the spring may be attached to or abut on a washer which is able to slide rotationally in relation to the dose setting member. The longitudinally compressible spring may extend coaxially with the piston rod or may be provided side by side with the piston rod. In one embodiment, a plurality of longitudinally compressible springs are provided side by side with the piston rod.

In another embodiment the spring is a helical spring which extends coaxially with the piston rod and which interconnects the second member and the dose setting member, such that rotation of the dose setting member to set the dose strains the spring rotationally, and so that translational displacement of the dose setting member and the piston rod to eject the dose results in rotation of the nut member to unstrain the spring. In a further embodiment, the spring is attached to the dose setting member and the second member such that it is strained rotationally and longitudinally, when the dose setting member is rotated in relation to the second member.

In order of increase the potential energy stored in the spring, the spring may be prestained when the dose setting member is in the predetermined position, so that, when the dose setting member is rotated, the spring is strained even more. In one embodiment, the ends of the helical spring are rotated at least three times in relation to each other so as to prestrain the spring rotationally, whereas in another embodiment the spring is rotated five times or ten times.

The syringe device may be designed, such that an outer dimension e.g. the diameter, of the spring decreases, when the dose setting member is moved in the proximal direction. Furthermore, the syringe device may be designed such that the outer dimension e.g. the diameter, of the spring is as large as possible, when the dose setting member is in its predetermined position and, thus, the spring is as close to the side wall of the syringe device as possible.

The cross-section of a winding of the spring may be quadrangular such that the bending resistance of the spring is as high as possible and, thus, the potential energy stored when the spring is twisted is as high as possible. In one embodiment, a radial dimension of a cross section of a winding of the helical spring is larger than an axial dimension of the cross section. For example the radial dimension may be five times larger than the axial dimension.

Three embodiments of the spring are described in the following. In a first embodiment, the spring is chosen such that it is not supposed to assist in the ejection, but merely serves the purpose of ensuring that the second member at any time abuts the stop surface. In a second embodiment, the spring is intended to assist the user during the ejection, such that, when the dose setting member is dialed up, enough potential energy is stored to reduce the force needed to perform an ejection. In this embodiment, the spring also serves the purpose of ensuring that the second member abuts the stop surface. Finally, in a third embodiment, the spring is chosen with characteristics which ensure that the user merely needs to initiate the ejection, whereafter the potential energy stored in the spring is high enough to perform the ejection.

The syringe device of the present invention may be designed such that the user may be able to pre-strain the spring such so as to change the syringe device between the three embodiments mentioned above.

In the present invention there is provided a first locking means for locking the first and second members against relative rotation, so that no displacement of the piston rod and the proximal direction is possible, when the first locking means is in its locking position. The first locking means may be moved between a locking and a non-locking position.

The first locking means may be provided as screw adapted to be screwed into engagement with an outer surface of the second member. The screw may be provided in the housing or the screw may be provided in the first member such that it may be screwed into engagement with the second member. The second member may comprise a plurality of grooves or indentations which the screw engage when it is in the locking position.

The first locking means may be adapted to lock the first member for rotation in relation to the second member, while allowing the members to move translationally in relation to each other. The first locking means may be provided as protrusions which extend radially from the first member in to a groove in the second member. Alternatively the first locking means may be provided as protrusions extending from the second member into the first member. The first locking means may be movable between a locking and a non-locking position. The first locking means may comprise a plurality of protrusions such as four, engaging a corresponding number of grooves. Alternatively the number of grooves exceeds the number of protrusions. The result is that the member e.g. the first member, comprising the movable protrusions need only to be rotated a small angle in relation to the other member e.g. the second member, in order to be positioned such that engagement with grooves is possible.

The syringe device may further comprise a second locking means adapted to lock the dose setting member such that no relative rotation of the dose setting member and the first member is possible when the second locking member is in its locking position and in such a way that the dose setting member can slide longitudinally relative to the first member.

The second locking member may be used to ensure that a set dose is not changed by accident prior to ejection. E.g. such that no relative rotation of the dose setting member and the first member is possible, when the second locking member is in its locking position, and in such a way that the dose setting member may slide longitudinally relative to the first member.

The second locking member may be provided as a screw or a pin adapted to engage a side portion of the dose setting member. In the latter embodiment, the dose setting member may comprise at least one groove to be engaged by the second locking member. In order to lock the dose setting member, the second locking member may be screwed or pushed from a non-engaging position into an engaging position, wherein at least a part of the second locking member extends into the groove. The groove may have a longitudinal extent allowing the pin or screw to engage the dose setting member at different longitudinal positions.

In the following a first embodiment of the invention will be described in further detail. In the first embodiment the housing comprises the first member.

An end surface of the second member may abut a stop surface of the first member when the first locking means is in its locking position. Accordingly, the first locking means may be provided as a lock nut which when tightened against the first member ensures that the piston rod may not rotate in relation to the first and second member. Thus surfaces of the first and second member are tightened in relation to each other.

As described in the aforementioned the dose setting member defines a passage for the piston rod, the passage having a threaded inner surface for engagement with the threaded outer surface of the piston rod, so as to define a connection between the dose setting member and the piston rod. Furthermore the dose setting member and the piston rod may be arranged in relation to each other such that a pure translational displacement of the dose setting member relative to the housing is transmittable via said connection into a pure translational displacement of the piston rod relative to the housing.

In some embodiments, the second member is able to be move relative to the piston rod between the stop surface and the piston, whereas in other embodiments, the second member is retained in relation to the first member, such that the longitudinal position of the second member relative to the first member is essentially fixed. The fixing of the second member may be achieved by providing the second member between the stop surface, which retains the second member in the proximal direction, and a further stop surface which retains the second member in the distal direction. In order to make it possible for the second member to rotate when the piston rod is moved longitudinally during ejection, the friction between the second member and the surfaces, which it abuts, should be as low as possible. Accordingly, the materials of the second member and/or of those members of the first member defining the aforementioned surfaces may be low friction materials, or there may be applied a reducing agent between the parts.

The stop surface may be provided on a retaining member adapted to retain the second member such that essentially no relative longitudinal displacement between the second member and the first member is possible. As an example, the second member may be provided between a proximal part and a distal part of the retaining member, with the distal part being connected to or integral with the first member. In another embodiment, the distal part and the proximal part are both connected to the first member.

In the following a second embodiment of the invention will be described in further detail. In the second embodiment the housing comprises the second member.

The dose setting member and the first member may be locked for relative translational movement, while allowing relative rotational movement. The lock for relative translational movement may be provided by means barbed portions engaging each other. The barbed portions may comprise engaging surfaced which are adapted to slide in relation to each other The second locking means may be provided as protrusions extending from the first member into a groove or an indentation in the dose setting member. Alternatively the second locking member may extend from the dose setting member into the first member. The second locking member may comprise a plurality of locking pins provided in grooves in the dose setting member and moveable between a non-locking position and a locking position. The locking pins may be operable from a push button.

Furthermore, there may be provided a coordinating mechanism for coordinating the locking position of the first and second locking means such that when the second locking means are locked the first locking means are unlocked and vice versa. E.g. the second locking means may be provided as locking pins moveable into the first member whereby the first locking means are moved from the locking position into the non-locking position.

In a second aspect the present invention relates to a syringe device comprising:
  a housing;
  a piston rod having a threaded outer surface, the piston rod
    being retained in relation to the first member in such a
    way that no relative rotation of the piston rod and the first
    member is possible and in such a way that the piston rod
    can slide longitudinally relative to the first member;
  a dose setting member defining a passage for the piston rod,
    the passage having a threaded inner surface for engagement with the threaded outer surface of the piston rod, so
    as to define a connection between the dose setting member and the piston rod, the dose setting member being arranged with respect to the piston rod such that rotation of the dose setting member causes the dose setting member to be displaced longitudinally along the piston rod, whereby a stroke length of the piston rod is defined by the longitudinal displacement of the dose setting member in a proximal direction relative to a predetermined position of the dose setting member, and such that a pure translational displacement of the dose setting member relative to the housing is transmittable via said connection into a pure translational displacement of the piston rod relative to the housing, and;

a second member defining a passage for the piston rod, the passage having a threaded inner surface for engagement with the threaded outer surface of the piston rod, at least one end surface of the second member being arranged to abut a stop surface of the first member, so that the piston rod is locked against displacement in the proximal direction when the surface of the second member abuts the stop surface of the first member.

In one embodiment the stop surface of the second member faces in the proximal direction and is adapted to abut a distal facing stop surface of the first member. The lock against displacement in the distal direction may be achieved by providing a frictional lock is provided between the abutting surfaces, when the piston rod is locked against displacement in the proximal direction. This may be achieved by rotating the first and second member relative to each other, until a predetermined surface pressure is achieved on each of the abutting surfaces. Thus in the case of a frictional lock, a predetermined frictional force must be overcome in order to allow the first and second member to rotate relative to each other.

In one embodiment the piston rod is solid. This enables a compact configuration, as for identical polar moments of inertia the diameter of a tubular element is larger than the diameter of a solid element.

The invention according to the second aspect of the invention may comprise any feature(s) and/or element(s) of the invention according to the first aspect of the invention and vice versa.

DESCRIPTION OF THE DRAWINGS

The invention will now be described in further detail with reference to the drawings, in which:

FIGS. 1A-1D show a simplified drawing of the principle underlying the present invention. The distal direction referred to in the above summary of the invention is indicated by arrow 102, and the proximal direction is indicated by arrow 104. The syringe device comprises a piston rod 106, a dose setting member 108 and a second member 110, the second member being embodied as a lock nut in the embodiment of FIGS. 1A-1D. The outer surface of the piston rod 106 is threaded, and the internal surfaces of the dose setting member 108 and the second member 110 define passages with corresponding inner threads. Accordingly, the dose setting member 108 and the second member 110 may rotate along the piston rod. The dose setting member 108 and the second member 110 are provided between an intermediate member 112 which defines a stop surface 114 on its distal side. The intermediate member 112 is secured relative to a hosing (not shown). The four drawings show different stages of an ejection.

FIG. 1A shows the syringe device before a dose has been set. In this situation, the second member 110 (the lock nut) abuts the stop surface 114, and the dose setting member 108 is in its predetermined position. The dose is set by rotating the dose setting member 108 along the piston rod 106 in the proximal direction (i.e. the direction of arrow 104), whereby the dose setting member is said to be dialed up. If the dose setting member 108 is dialed too far in the proximal direction, it may be dialed down with an ejection needing to be performed. In FIG. 1B, the dose setting member 108 has been dialed to the desired position, e.g. such that a dose of 60 IU is set, and the user may perform an ejection by applying a longitudinal force in the distal direction to the dose setting member 108 or to the proximal end 116 of the piston rod 106. As the dose setting member 108 and the piston rod 106 are both threaded, a translational force e.g. in the distal direction, is transferred to the piston rod.

In FIG. 1C, the ejection has been performed and the dose setting member 108 is in its predetermined position. However, now the second member 110 does not abut the stop surface 114. Thus, in order to ensure that the piston rod 106 is not moved in the proximal direction, the second member 110 is rotated back along the piston rod until it abuts the stop surface. This results in the situation of FIG. 1D. The procedure describe above with reference to FIGS. 1A-1D may now be repeated, i.e. a new dose may be set and ejected.

As shown in FIGS. 2A-2D, a pre-strained helical spring 118 may interconnect the dose setting member 108 and the second member 110. When the dose setting member 108 is dialed up, i.e. moved from the position of FIG. 2A to the position of FIG. 2B, the spring is strained. Accordingly, when the ejection is performed, the spring rotates the second member 110 (the lock nut), such that it at all times abuts the stop surfaces 114, whereby the situation of FIG. 2C will never occur, FIG. 2C being included for illustrative purposes only. This ensures that the piston rod may only be moved in the distal direction. The potential energy stored in the spring as a result of the dialing up the dose setting member results in an assisting force for pushing the piston rod 106 forward, when the ejection is performed.

It will be appreciated from the description of FIGS. 2A-2D that the dose setting member 108 should be locked against rotation during ejection in order to ensure that the dose setting member is not dialed down by the strained spring 118. Accordingly, as shown in FIGS. 3A and 3B, the may be provided a dose lock 120, which may e.g. be in the form of a screw. A tip 122 of the screw engages a groove 124 of the dose setting member 108. As shown in FIG. 3B, there is provided a plurality of grooves provided along the circumference of the dose setting member. In order to allow the dose setting member 108 to move translationally during an ejection, the dose setting member, the grooves 124 have a longitudinal extent, cf. FIG. 3A, so that the dose setting member may slide in the distal direction, while the dose lock 120 prevents the dose setting member from rotating.

Furthermore, in order to ensure that the second member is not rotated when the dose setting member strains the spring, a second member lock 126 is provided. The second member lock 126 is adapted to engage the second member.

Figure 1A:
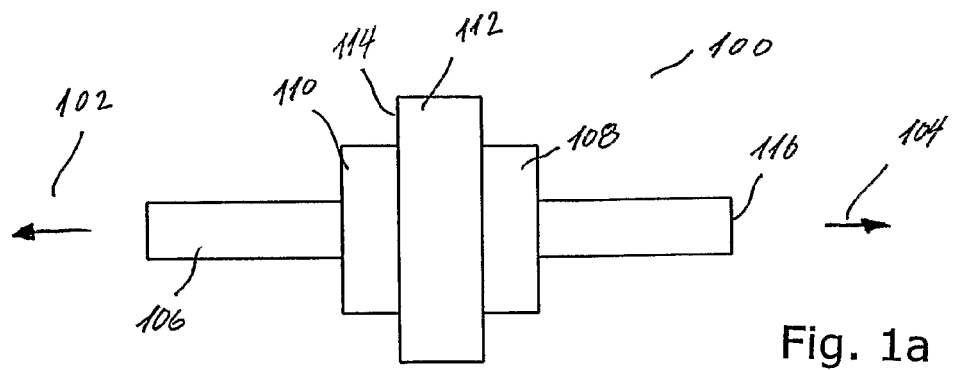
FIGS. 1A-1D illustrate the basic working principle of a first embodiment of the syringe device according to the present invention.
Figure 1B:
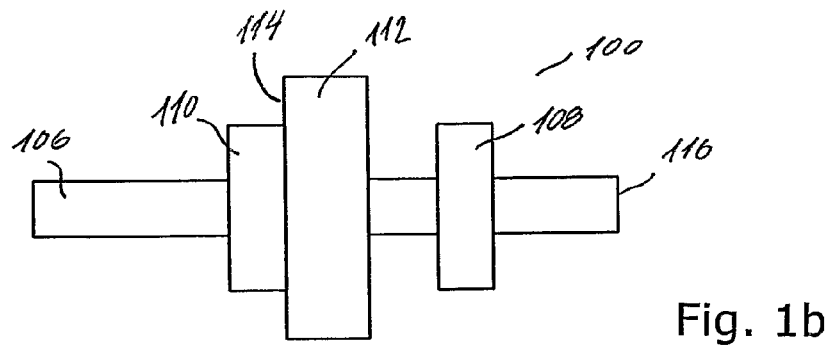
Figure 1C:
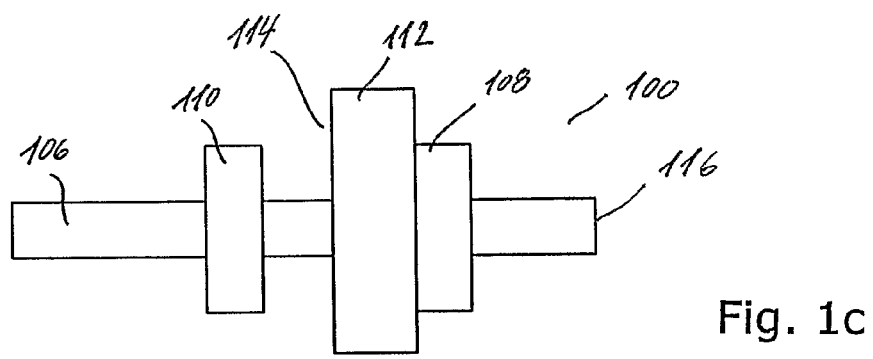
Figure 1D:
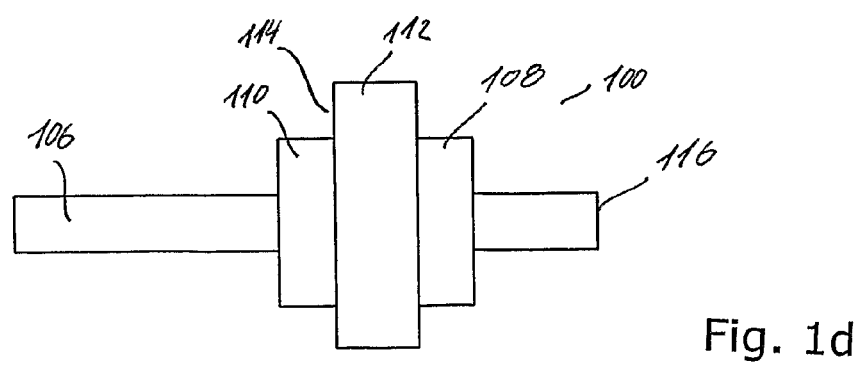
Figure 2A:
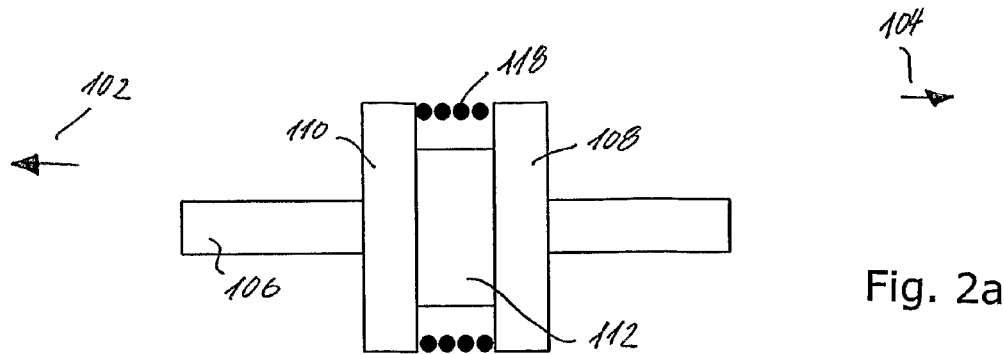
FIGS. 2A-2D illustrate a first embodiment of an ejection assistance system of a syringe device of the present invention.
Figure 2B:
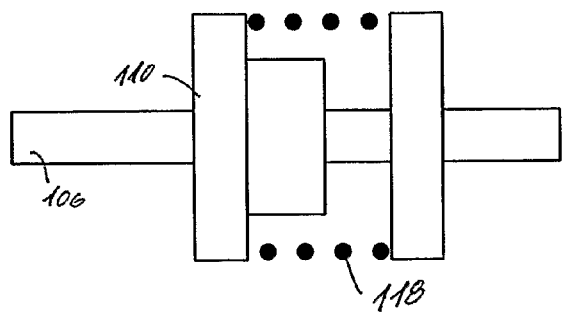
Figure 2C:
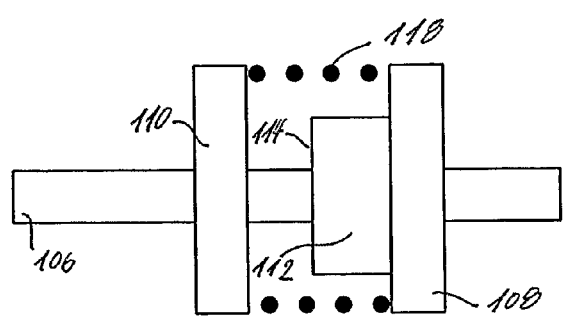
Figure 2D:
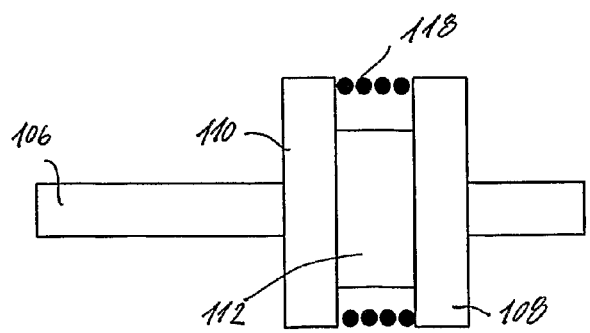
Figure 3A:
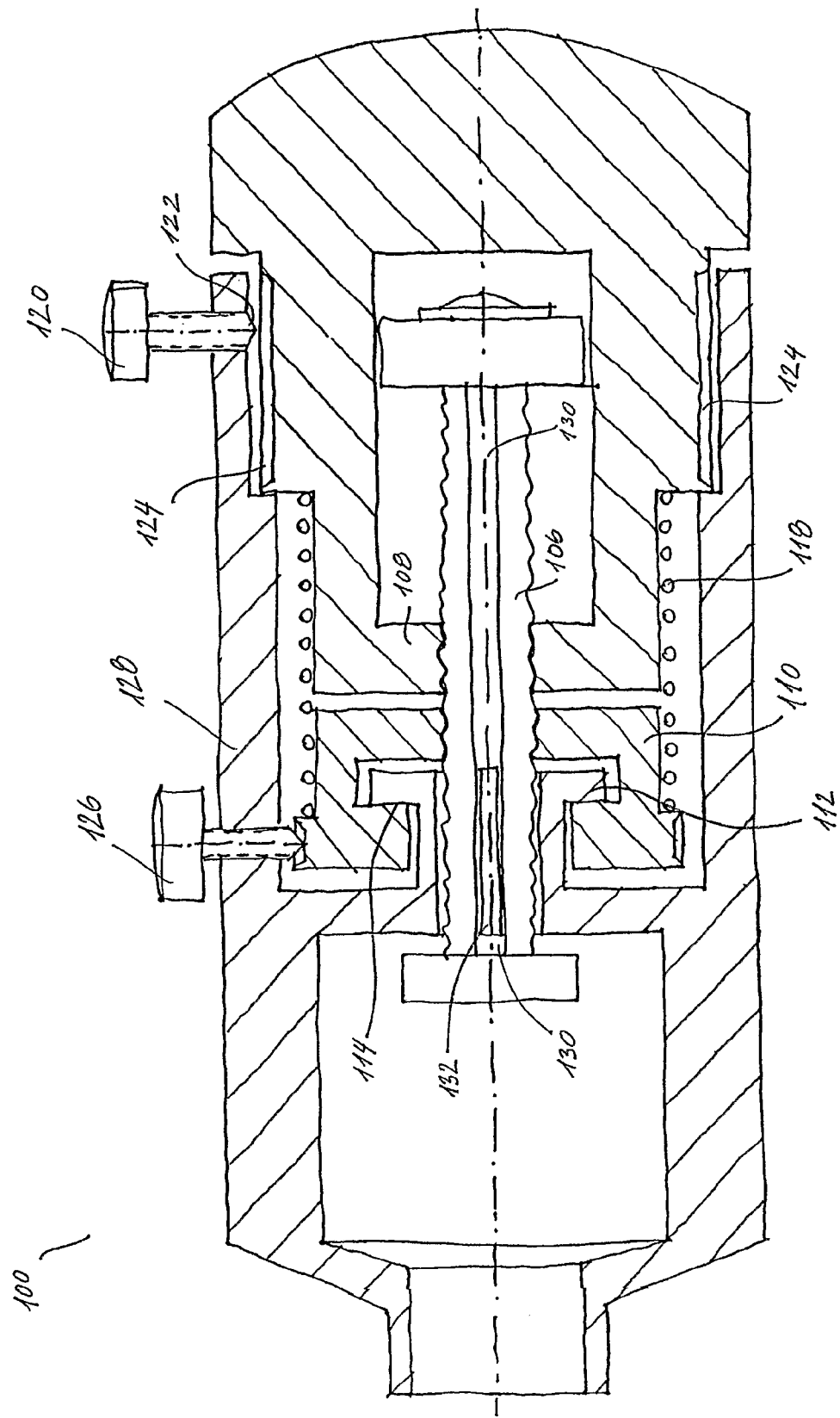
FIGS. 3A-3B show an embodiment of the ejection assistance system comprising locking members for locking the dose setting member and the second member for rotation.
Figure 3B:
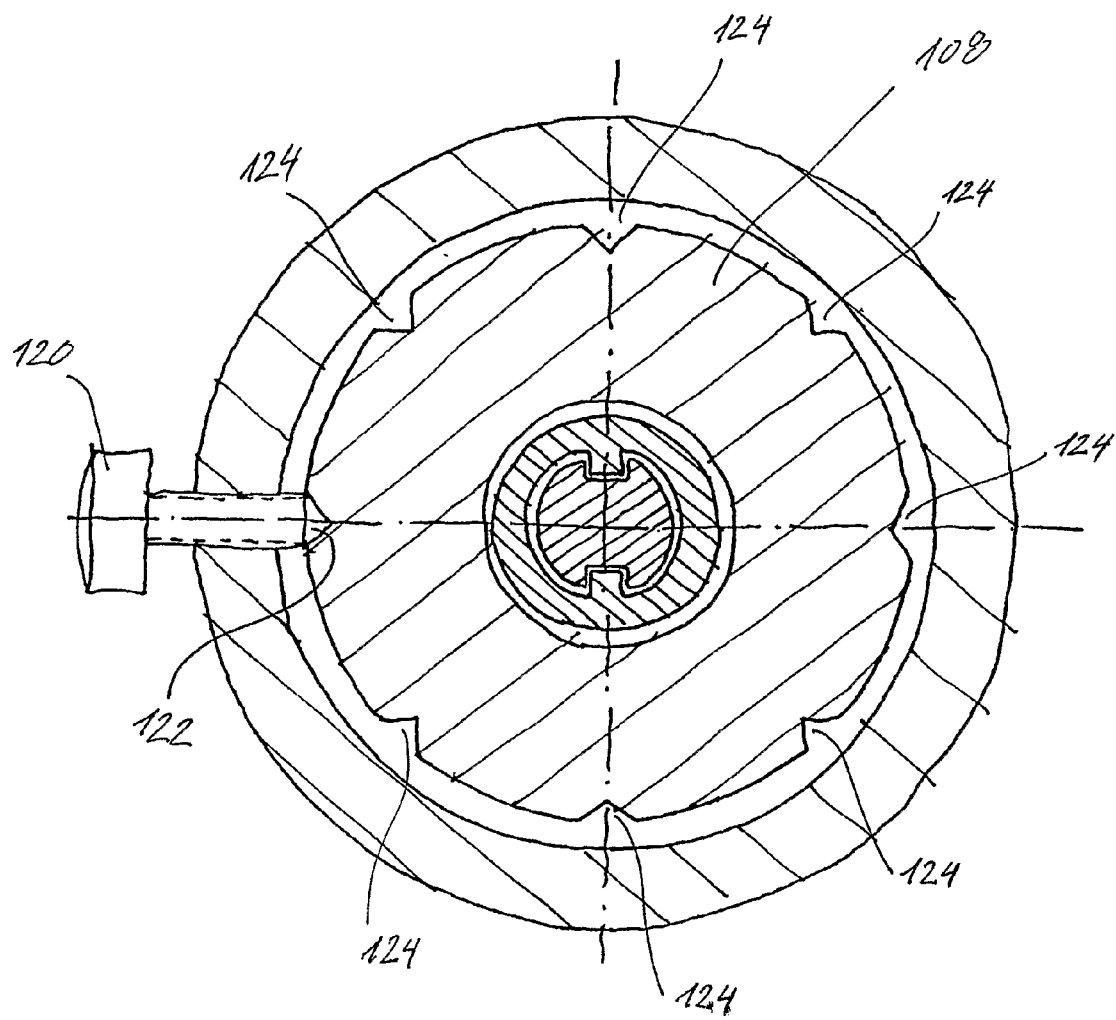

In FIG. 3A, intermediate member 112 is adapted to retain the second member, such that essentially no longitudinal displacement of the second member relative to the first member 128 is possible. The intermediate member 112 is integral with the first member and defines an inwardly projecting collar portion of the first member. The piston rod 106 is provided with a linear track 130 which is engaged by a protrusion 132 secured to or integral with the first member, whereby the piston rod 106 is locked against rotation relative to the first member.

FIGS. 4A-4G illustrate the working principle of a second embodiment of the device according to the present invention. Piston rod has a threaded outer surface which extends through second member 210 and engages an inner thread thereof. First member 212 defines a bore for the piston rod 206, there being however no engagement between the thread of piston rod 206 and the bore in the first member 212. Dose setting member 208 defines a threaded passage for engagement with the thread of piston rod 206. The first member 212 is translationally secured to dose setting member 208, and the first member 212 is rotationally locked in relation to the piston rod 206. As indicated by bar 250, first member 212 is locked for rotation in relation to second member 210. A distal end of pre-strained helical spring 218 is secured to the second member 210, and a proximal end of the spring 218 is secured to the dose setting member 208. The Bars 252, 254 and 256 illustrate the rotation position of the dose setting member 208, the first member 212 and the piston rod 206, respectively.

Figure 4A:
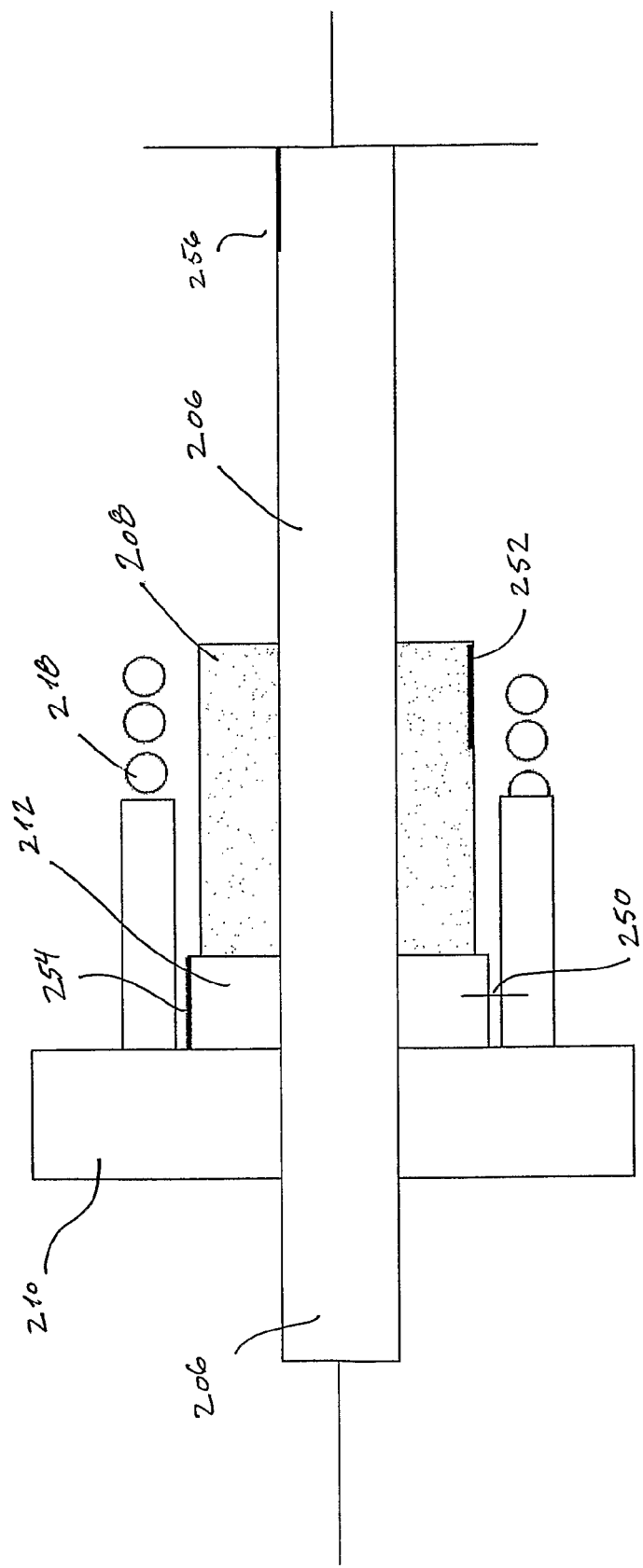
FIGS. 4A-4G illustrates the working principle of a second embodiment of the syringe device according to the present invention, and FIGS. 5A-5F and 6 illustrated a second embodiment of the syringe device of the invention.
Figure 4B:
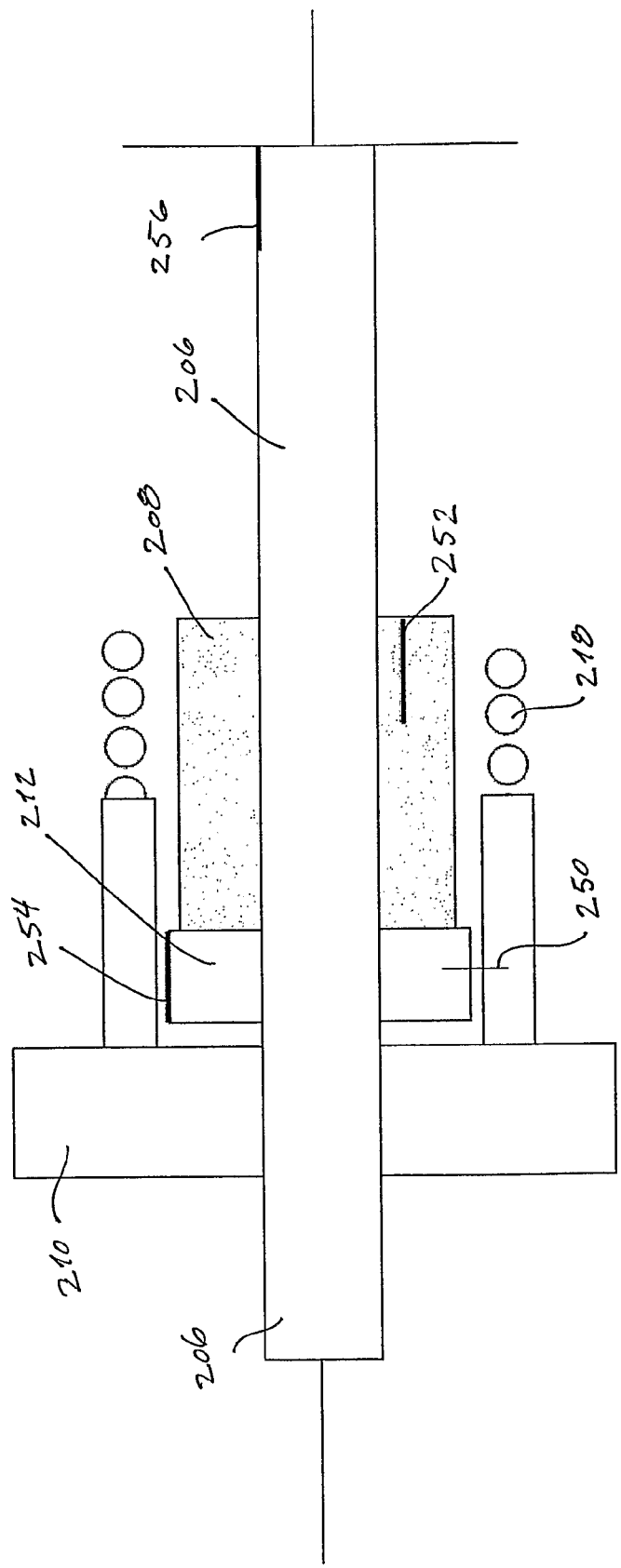
Figure 4C:
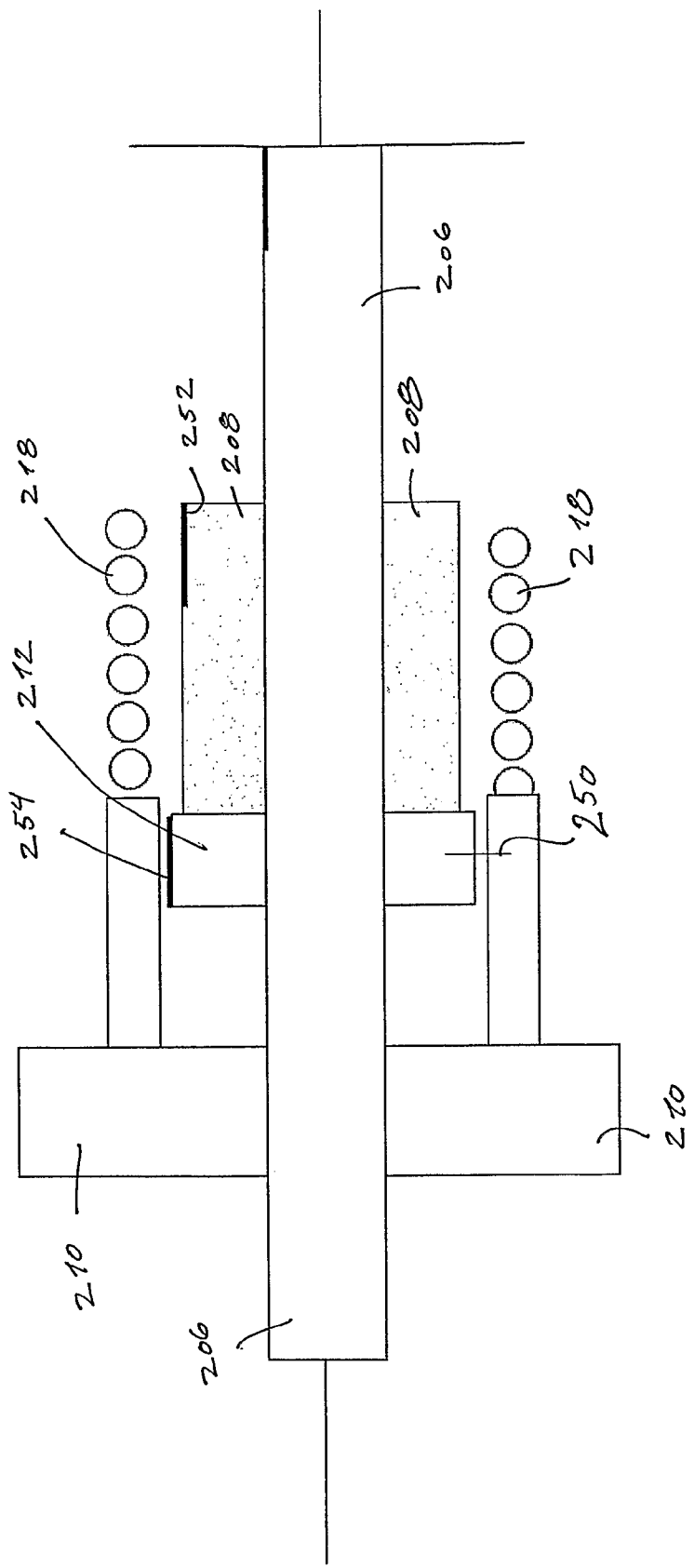
Figure 4D:
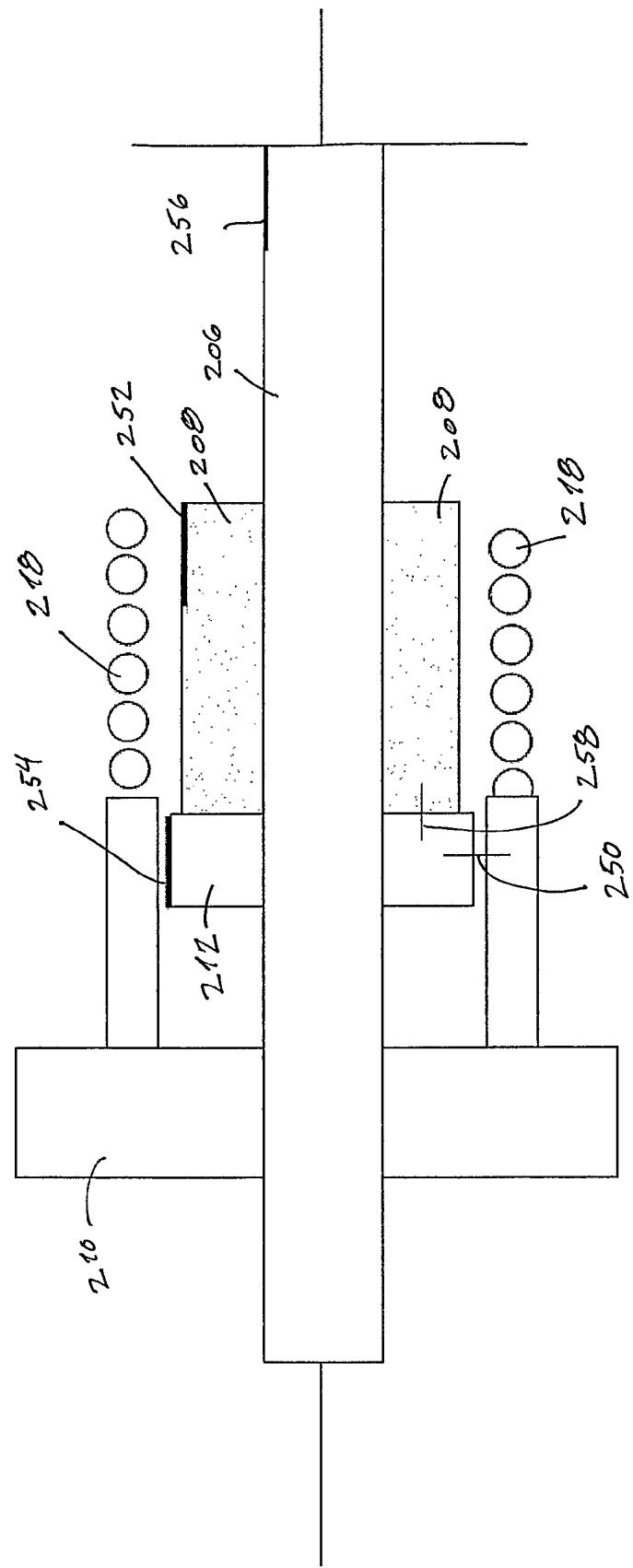
Figure 4E:
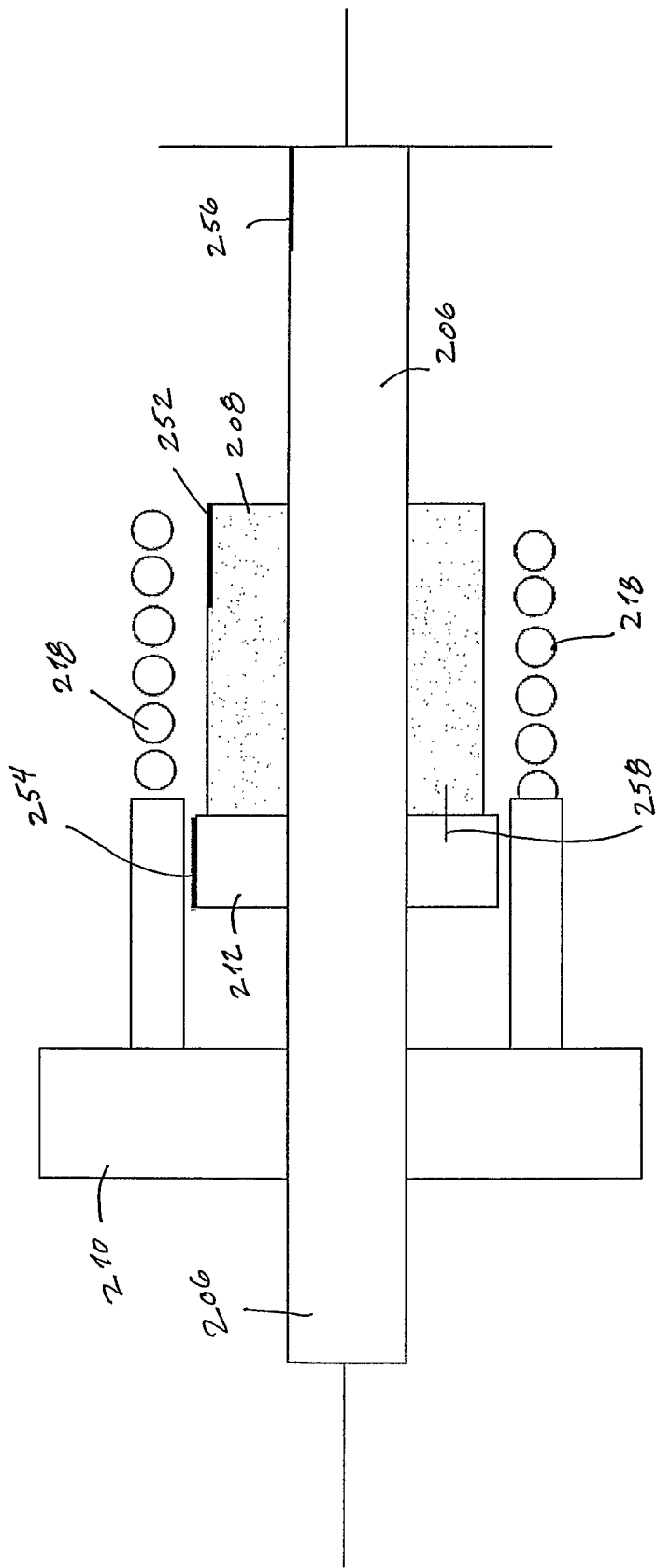
Figure 4F:
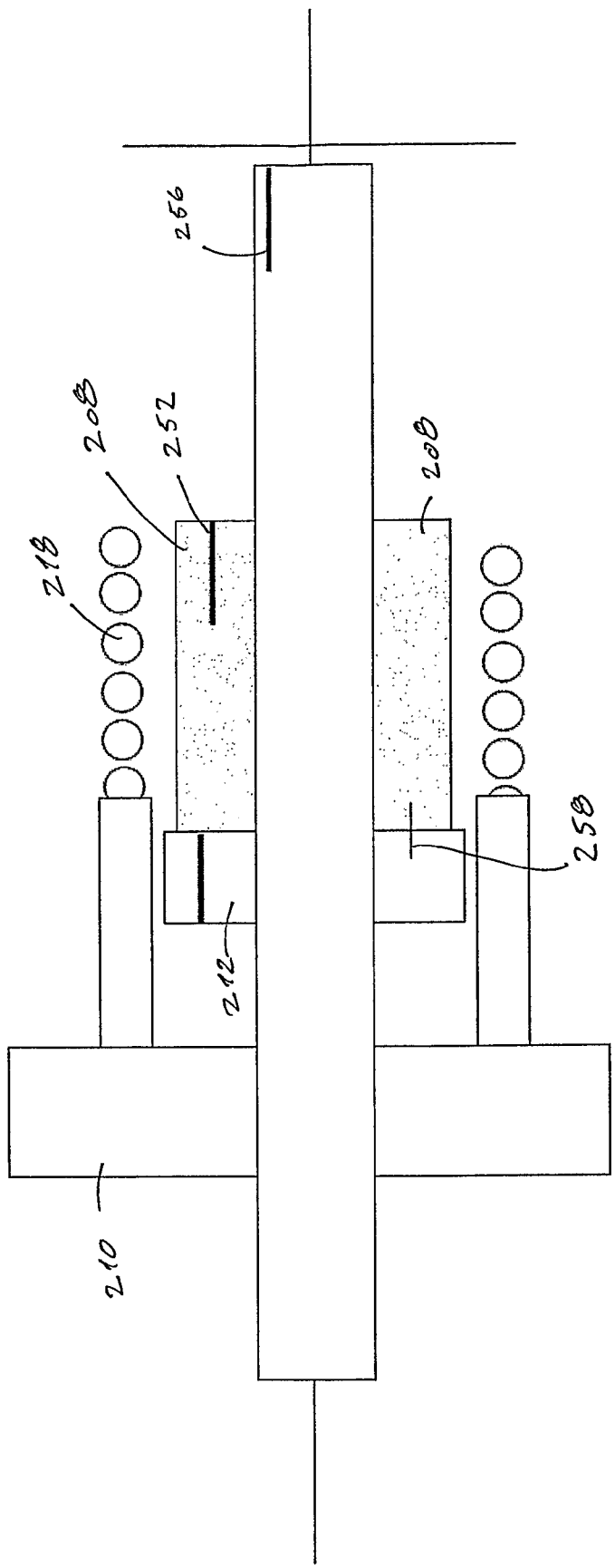

FIG. 4A illustrates an initial position of the device. In FIG. 4B, dose setting member 208 has been dialed up, i.e. rotated relative to piston rod 206, as illustrated by bar 252. Second member 210, which is rotationally locked in relation to first member 212, has rotated with the dose setting member and first member 212, and spring 218 has been strained. In FIG. 4C, dose setting member 208 has been dialed further up, resulting in further straining of spring 218. Subsequently, as illustrated by bar 258 in FIG. 4D, dose setting member 208 is rotationally locked to first member 212, and as illustrated in FIG. 4E the rotational lock between first member 212 and second member 210 is released (the bar 250 appearing in FIG. 4D being removed in FIG. 4E).

Figure 4G:
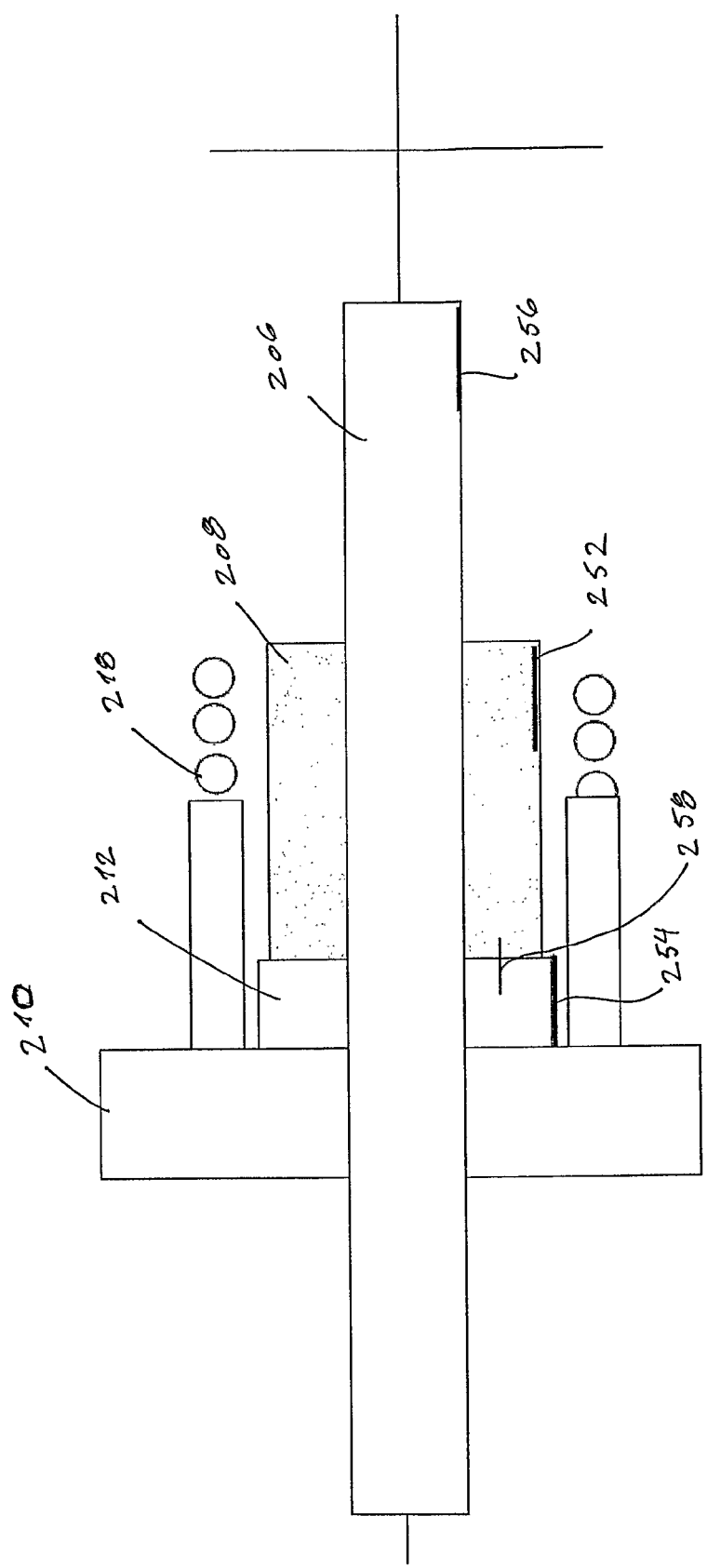

As dose setting member 208 is dialed down to eject a dose from the syringe device, first member 212 rotates with the dose setting member 208, and piston rod 206 rotates with the first member, as the first member 212 is rotationally locked to the piston rod. Potential energy stored in the helical spring 218 is released and provides a force for easing ejection. In FIG. 4G, dose ejection has completed, and the dose setting member 208 and first member 212 are dialed entirely down.

Figure 5A:
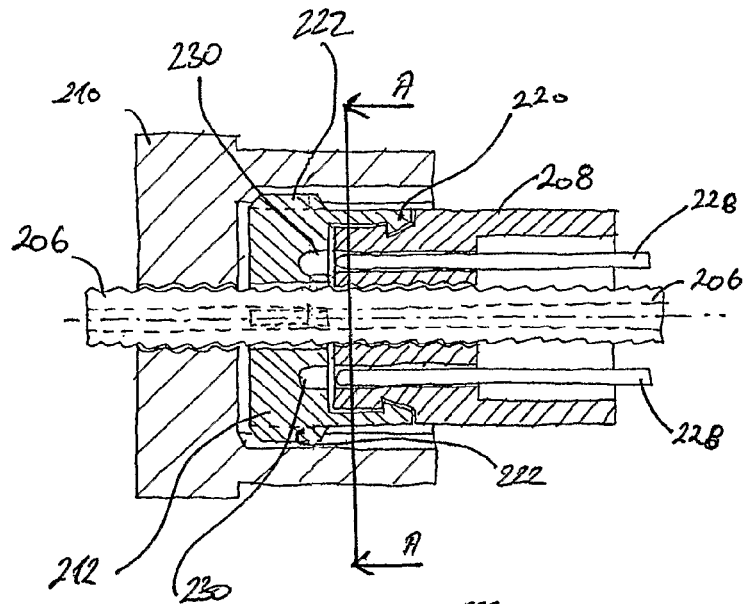
Figure 5B:
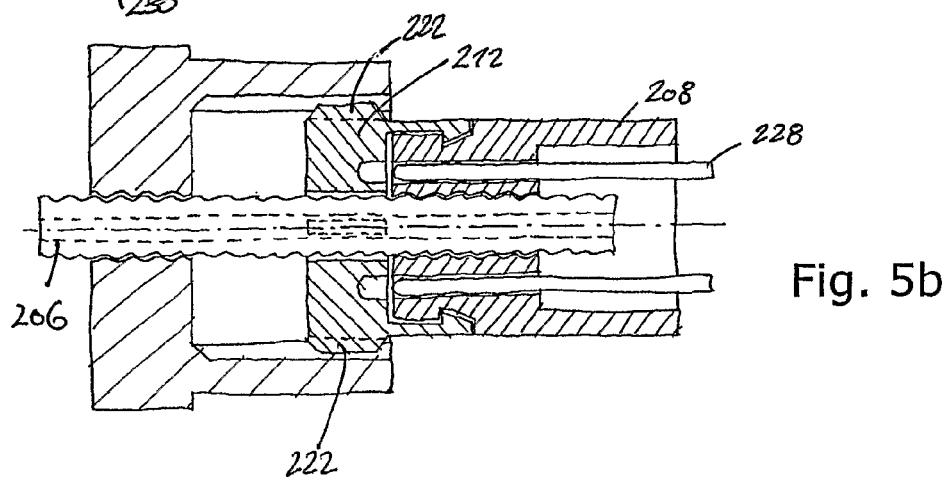
Figure 5C:
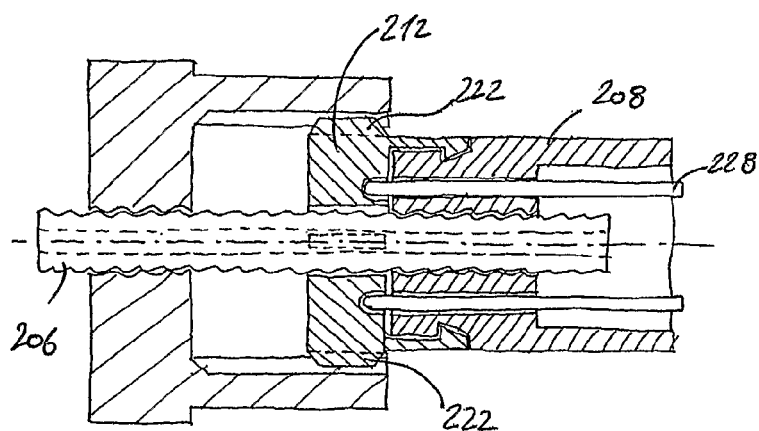
Figure 5D:
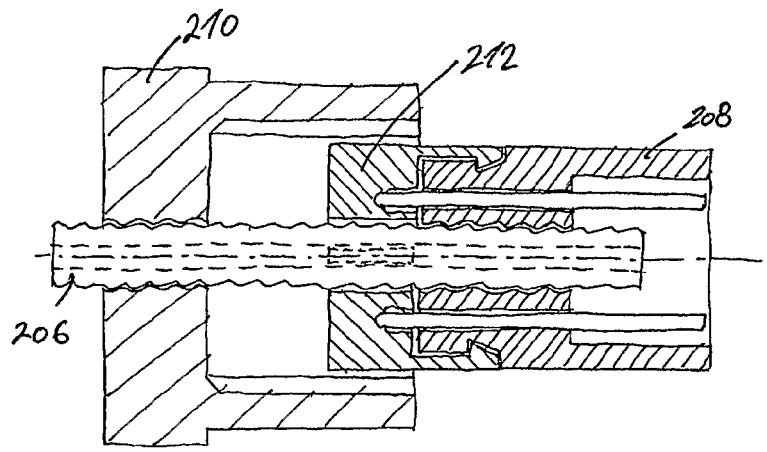
Figure 5E:
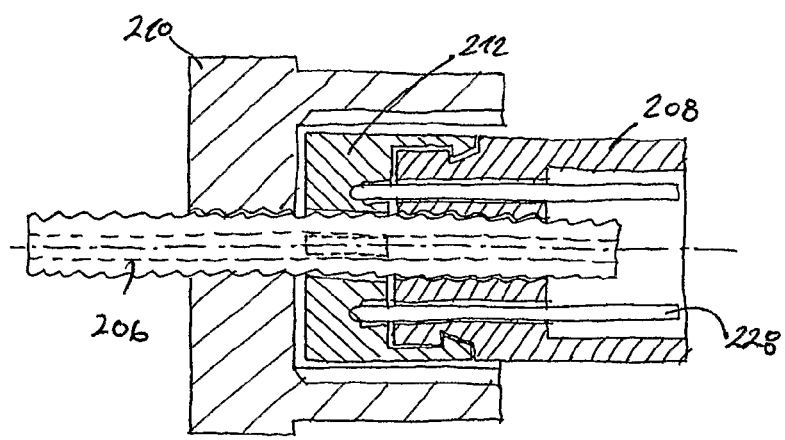
Figure 5F:
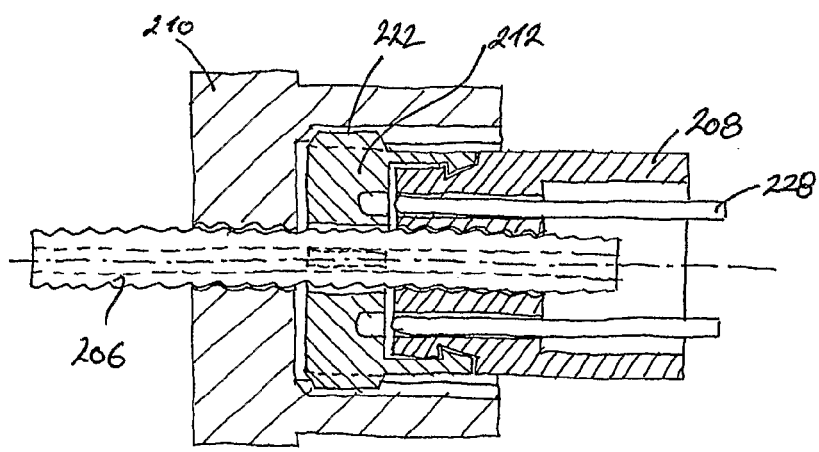
Figure 6:
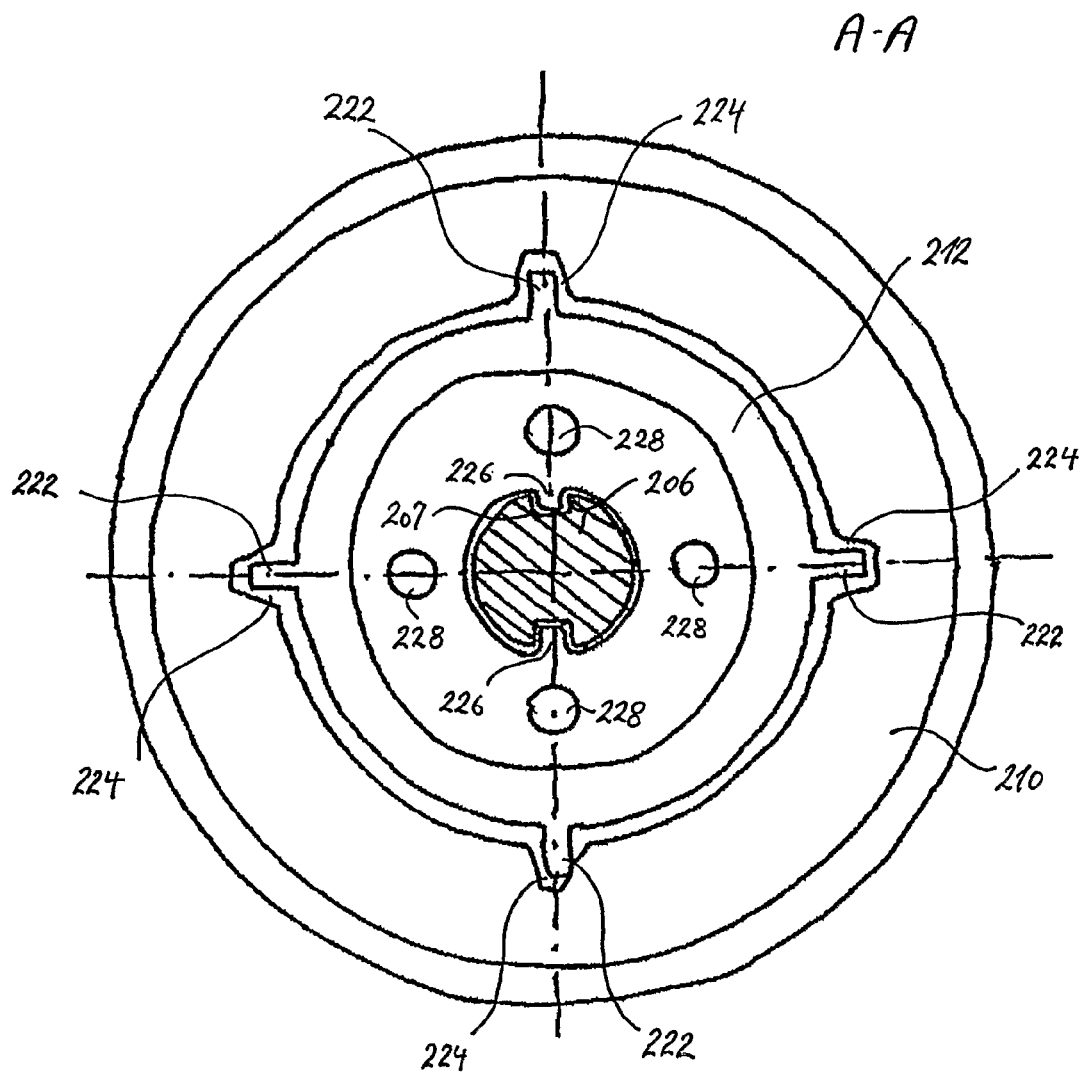

FIGS. 5A-5F and 6 illustrate an embodiment embodying the working principle of FIGS. 4A-4G. First member 212 engages dose setting member 208 via barbed portion 220, and as illustrated in the cross-sectional view of FIG. 6, first member 212 engages second member 210 via protrusions 222 which are arranged to slide in grooves 224 formed in the second member 210. Thereby, second member 212 is rotationally locked relative to the first member 210. In FIG. 6, the protrusions 222 are shown in a projected position, in which provide a rotational lock for preventing first member 212 from rotating relative to the second member 210. The rotational lock may be released by withdrawing the protrusions 222 from their projecting position to a retracted position. Protrusions 226 provided on the first member 212 engage grooves 207 in piston rod 206 to rotationally lock the first member 212 in relation to the piston rod 206. FIGS. 5A-5F further illustrate locking pins 228 for engaging cut-outs 230 to provide a rotational lock between dose setting member 208 and first member 212. In FIGS. 5A, 5B and 5F, the locking pins 228 do not engage the cut-outs 230 in the first member 212, whereas in FIGS. 5C-5E, the locking pins provide the described rotational lock.

FIG. 5A illustrates an initial position of the syringe device. In FIG. 5B, dose setting member 208 has been dialed up along piston rod 206, and the first member 212 has been translationally displaced along the piston rod with the dose setting member, whereby at relative rotational movement between the dose setting member 208 and the first member 212 has occurred. In FIG. 5C, locking pins 228 have been brought into engagement with the first member 212, e.g. as a result of a user action, such as a button push, having been performed. In FIG. 5D, protrusions 222 have been withdrawn from their projecting position, so that the first member 212 may rotate freely in relation to the second member 210. Dose setting member 208 is forced forwardly (i.e. in a distal direction), thereby advancing the piston rod 206 from ejecting a dose. FIG. 5E illustrates the resulting position, in which the first member 212 and the dose setting member 208 are back in their initial position. In FIG. 5F, protrusions 222 are back in their projected position, and locking pins 228 have been released from the first member 212, and a new dose may be set and ejected. It will be appreciated that the position of FIG. 5F is identical with the position of FIG. 5A, except that the piston rod 206 is more advanced in FIG. 5F than in FIG. 5A, corresponding to the dose set and ejected as described above. A helical spring as described in relation to FIGS. 4A-4G for providing an ejecting force, in addition to the force provided by a user to the dose setting member 208, may also be employed in the embodiment of FIGS. 5A-5F, though not shown.

I claim:

1. A syringe device comprising:
   a housing;
   a first member (112, 212) that is axially fixed to the housing;
   a piston rod (106;206) having a threaded outer surface, the piston rod (106;206) being retained in relation to the first member(112;212) in such a way that no relative rotation of the piston rod (106;206) and the first member (112; 212) is possible and in such a way that the piston rod (106;206) can slide longitudinally relative to the first member (112;212);
   a dose setting member (108;208) defining a passage for the piston rod (106;206), the passage having a threaded inner surface for engagement with the threaded outer surface of the piston rod (106;206), so as to define a connection between the dose setting member (108;208) and the piston rod (106;206), the dose setting member (108;208) being arranged with respect to the piston rod (106;206) such that rotation of the dose setting member (108;208) causes the dose setting member (108;208) to be displaced longitudinally along the piston rod (106; 206), whereby a stroke length of the piston rod (106; 206) is defined by the longitudinal displacement of the dose setting member (108;208) in a proximal direction (104) relative to a predetermined position of the dose setting member (108;208), and such that a translational displacement of the dose setting member (108;208) relative to the housing is transmittable via said connection into a translational displacement of the piston rod (106; 206) relative to the housing;
   a second member (110;210) defining a passage for the piston rod (106;206) the passage having a threaded inner surface for engagement with the threaded outer surface of the piston rod (106;206), and;

a first locking means (126;250) for locking the first member (112;212) and second member (110;210) against relative rotation, so that no displacement of the piston rod (106;206) in the proximal direction (104) is possible, when the first locking means (126;250) is in its locking position, characterized by a spring (118;218) which interconnects the second member (110;210) and the dose setting member (108;208) and biases them towards each other, such that when the dose setting member (108;208) is rotated and thereby displaced longitudinally along the piston rod (106;206), the spring is strained, and such that translational displacement of the dose setting member (108;208) and the piston rod (106;206) in the distal direction (102) to eject the dose unstrains the spring (118;218), whereby energy accumulated during straining of the spring (118;218) is released to provide said ejection force.

2. A syringe device according to claim 1, wherein the spring (118;218) is a helical spring (118;218) which extends coaxially with the piston rod (106;206) and which interconnects the second member (110;210) and the dose setting member (108;208), such that rotation of the dose setting member (108;208) to set the dose, strains the spring (118;218) rotationally, and so that translational displacement of the dose setting member (108;208) and the piston rod (106;206) to eject the dose results in rotation of the second member (110;210) to unstrain the spring.

3. A syringe device according to claim 1, wherein the spring (118;218) is prestrained when the dose setting member (108;208) is in the predetermined position.

4. A syringe device according to claim 1, wherein the spring (118;218) forms part of an ejection assisting system (118;218) which is adapted to force the piston rod (106;206) in the distal direction so as to eject the dose, without the aid of the user, when the user has initiated the ejection.

5. A syringe device according to claim 1, further comprising a second locking means (120;258) adapted to lock the dose setting member (108;208) such that no relative rotation of the dose setting member (108;208) and the first member (112;212) is possible when the second locking means (120;258) is in its locking position and in such a way that the dose setting member (108;208) can slide longitudinally relative to the first member (112;212).

6. A syringe device according to claim 1, wherein an end surface of the second member (110) abut a stop surface (114) of the first member (112) when the first locking means (126) is in its locking position.

7. A syringe device according to claim 1, wherein a pure translational displacement of the dose setting member (108) relative to the housing is transmittable via said connection into a pure translational displacement of the piston rod (106) relative to the housing.

8. A syringe device according to claim 1, wherein the second member (110) is retained in relation to the first member (112) such that the longitudinal position of the second member (110) relative to the first member (112) is essentially fixed.

9. A syringe device according to claim 1, wherein a stop surface (114) is provided on a retaining member (112) adapted to retain the second member (110) such that essentially no relative longitudinal displacement between the second member (110) and the first member (112) is possible.

10. A syringe device according to claim 9, wherein the second member is provided between a proximal part and a distal part of the retaining member and wherein the distal part is connected to the first member.

11. A syringe device according to claim 1, wherein the housing comprises the first member (112).

12. A syringe device according to claim 1, wherein the dose setting member (208) and the first member (212) are locked for relative translational movement.

13. A syringe device according to claim 12, further comprising a coordinating mechanism (228,230,222) for coordinating the locking position of the first and second locking means (250,258) such that when the second locking means (258) are locked, the first locking means (250) are unlocked and vice versa.

14. A syringe device according to claim 1, wherein the housing comprises the second member (210).

15. A syringe device comprising:

a housing;

a first member that is axially fixed to the housing;

a piston rod (106) having a threaded outer surface, the piston rod (106) being retained in relation to the first member (112) in such a way that no relative rotation of the piston rod (106) and the first member (112) is possible and in such a way that the piston rod (106) can slide longitudinally relative to the first member (112);

a dose setting member (108) defining a passage for the piston rod (106), the passage having a threaded inner surface for engagement with the threaded outer surface of the piston rod (106), so as to define a connection between the dose setting member (108) and the piston rod (106), the dose setting member (108) being arranged with respect to the piston rod (106) such that rotation of the dose setting member (108) causes the dose setting member (108) to be displaced longitudinally along the piston rod (106), whereby a stroke length of the piston rod (106) is defined by the longitudinal displacement of the dose setting member (108) in a proximal direction (104) relative to a predetermined position of the dose setting member (108), and such that a pure translational displacement of the dose setting member (108) relative to the housing is transmittable via said connection into a pure translational displacement of the piston rod (106) relative to the housing, and;

a second member (110) defining a passage for the piston rod (106), the passage having a threaded inner surface for engagement with the threaded outer surface of the piston rod (106), characterized by at least one end surface of the second member (110) being arranged to abut a stop surface (114) of the first member (112), so that the piston rod (106) is locked against displacement in the proximal direction (104) when the surface of the second member (110) abuts the stop surface (114) of the first member (112).

16. A syringe device according to claim 15, wherein a frictional lock is provided between the abutting surfaces, when the piston rod (106) is locked against displacement in the proximal direction (104).

17. A syringe device according to claim 15, wherein the piston rod (106) is solid.

18. A syringe device according to claim 15, further comprising a second locking means (120) adapted to lock the dose setting member (108) such that no relative rotation of the dose setting member (108) and the housing is possible when the second locking means (120) is in its locking position and in such a way that the dose setting member (108) can slide longitudinally relative to the housing.

19. A syringe device according to claim 15, further comprising a first locking means (126) adapted to lock the second member (110) such that no relative rotation of the second member (110) is possible when the first locking means (126) is in its locking position.

20. A syringe device according to claim 15, further comprising an ejection assisting system (118) for providing an ejection force for assisting an operator of the device in forcing the piston rod (106) in the distal direction so as to eject a dose.

21. A syringe device according to claim 20, wherein the ejection assisting system (118) is adapted to force the piston rod (106) in the distal direction so as to eject the dose, without the aid of the user, when the user has initiated the ejection.

22. A syringe device according to claim 20, wherein the ejection assisting system (118) comprises a spring (118) which is arranged to bias the second member (110) and the dose setting member (108) towards each other, such that when the dose setting member (108) is rotated and thereby displaced longitudinally along the piston rod (106), the spring (118) is strained, and such that translational displacement of the dose setting member (108) and the piston rod (106) in the distal direction to eject the dose unstrains the spring (118), whereby energy accumulated during straining of the spring (118) is released to provide said ejection force.

* * * * *